United States Patent [19]

Nielsen et al.

[11] Patent Number: 5,011,864

[45] Date of Patent: * Apr. 30, 1991

[54] WATER ABSORBENT LATEX POLYMER FOAMS CONTAINING CHITOSAN (CHITIN)

[75] Inventors: Steven F. Nielsen, Charlotte, N.C.; Dai W. Kim, Chatham, N.J.

[73] Assignee: Hoechst Celanese Corp., Somerville, N.J.

[ * ] Notice: The portion of the term of this patent subsequent to Feb. 5, 2008 has been disclaimed.

[21] Appl. No.: 533,243

[22] Filed: Jun. 4, 1990

Related U.S. Application Data

[63] Continuation-in-part of Ser. No. 434,376, Nov. 9, 1989.

[51] Int. Cl.⁵ .................................................. C08J 9/28
[52] U.S. Cl. ........................................ 521/70; 521/841; 521/139; 521/140; 521/134
[58] Field of Search ................ 521/70, 84.1, 134, 139, 521/140

[56] References Cited

U.S. PATENT DOCUMENTS

| | | | |
|---|---|---|---|
| 3,959,197 | 5/1976 | Salyer et al. | 54/59 |
| 4,000,028 | 12/1976 | Moey | 521/69 |
| 4,076,663 | 2/1978 | Masuda et al. | 525/54.31 |
| 4,497,930 | 2/1985 | Yamasaki et al. | 525/54.24 X |
| 4,910,250 | 3/1990 | Saotome | 524/556 |

*Primary Examiner*—Morton Foelak
*Attorney, Agent, or Firm*—Lynch, Cox, Gilman & Mahan

[57] ABSTRACT

A water absorbent latex polymer foam produced by the process of combining a foamed latex polymer product with both a water absorbent polymer and chitin and drying that blend to form a foamable latex polymer containing both water absorbent polymer and chitin. The latex foams produced by this process are of great use, for example, with wound or surgical dressings.

25 Claims, No Drawings

WATER ABSORBENT LATEX POLYMER FOAMS CONTAINING CHITOSAN (CHITIN)

CROSS REFERENCE TO RELATED APPLICATIONS

This application is a continuation-in-part of application Ser. No. 434,376 filed on Nov. 9, 1989, now allowed.

BACKGROUND OF INVENTION

1. Field of Invention

This invention discloses water absorbent polymer articles and a process for their production. More particularly, the invention discloses a latex polymer foam containing both a water absorbent polymer and chitosan (chitin) (hereinafter reference to "Chitin" or "Chitoson" will include both) within its structure.

2. Prior Art

Recently there has been interest in producing products which are highly absorbent of aqueous fluids, particularly blood and exudate, as drying materials, wound dressings, and chromatographic materials and for other similar uses. Some of the prior art materials used to form these products have been non-woven fabrics, papers, pulps, spongy urethane resins, natural sponges and the like. However, these materials exhibit relatively low water absorbency, thus failing to satisfy the need for a low volume, highly water absorbent product.

Substitutes for these materials such as cross-linked polyethylene oxides, cross-linked polyvinyl alcohols and hydrolyzed products of starch-polyacrylonitrile-grafted polymers have recently appeared on the market. While these products do show increased water absorbency, it is still not sufficiently high to justify the increased costs and difficulty of production. In addition, some of these materials create disposal problems because they are not biologically degradable.

Japanese Patent Application Kokai, No. 57-92,032 (1982) discloses a polyurethane foam that contains a useful water absorbent polymer wherein the size of the water absorbent resin is in the range from about 200 to 400 microns.

A biodegradable, highly water absorbent resin is disclosed in U.S. Pat. No. 4,076,663. While the resins of this patent do show increased water absorbency, their use has been limited to mixing them in sanitary napkins, diapers and other such products wherein the resins are used in their particulate or powder form.

U.S. Pat. Nos. 4,454,268, 4,337,181 and 4,133,784 disclose various types of films partially comprised of water absorbent polymers. These patents disclose starch-based, water absorbent polymers prepared from a combination of starch and ethylene acrylic acid copolymers.

U.S. Pat. No. 3,669,103 discloses water swellable, water insoluble polymeric sorbents for the absorption of aqueous fluids wherein said polymeric sorbents are lightly cross-linked polymers. This patent discloses the use of a polyurethane foam as a support for the polymeric absorbent.

Latex materials, particularly latex foams have been well known for many years. For example, the largest single use of latex today is in foam rubber. Latex foams are frequently used in mattresses, pillows, seat cushions, carpet backing and textile foam laminates. Latex foams also find use as cushioning in many types of fabrics such as athletic clothing.

There are numerous processes for the production of latex foams. See for example, U.S. Pat. Nos. 3,650,995, 4,205,103, and 4,174,415. While numerous latex foam patents exist, none disclose the use of a latex foam containing within its structure both a cellulose-based water absorbent polymer and chitin or a process for production of such a material.

One of the newest uses for super absorbent materials is as a wound dressing or covering for injuries. Chitin or its deacylated form, chitosan, have also been useful as biopolymeric powders to assist in the treatment of wounds and injuries. Chitosan is a glucosaminoglycan which is a major constituent of the shells of shrimp, crabs and lobsters, the cell walls of filamentous fungi and the exoskeletons of insects. The use of chitosan as a biopolyermic powder has been described, for example, by several patents by Balassa. See U.S. Pat. Nos. 3,903,268, 3,911,116 and 3,914,413. Other patents disclosing the use of chitosan and describing some of its properties include U.S. Pat. Nos. 4,018,678, 4,609,470, 4,613,502 and 4,659,700.

In the medical field chitosan powder acts as a biopolymeric regeneration material. It very slowly depolymerizes in a wound with its monomeric components efficiently entering into a metabolic reaction in the wound. The powder contributes in this way to the regeneration of damaged skin tissue.

Because of the biopolymeric features of chitosan, it is not surprising that it has been combined with various materials specifically for use as wound dressings. For example, U.S. Pat. No. 4,460,642 discloses the use of a polytetrafluoroethylene fibril matrix which contains hydrophilic absorbents including chitin and chitosan.

The use of chitosan with gelatin to form a surgical dressing or wound dressing to assist the healing process is also disclosed in U.S. Pat. No. 4,572,906. The combination of a polyvinyl alcohol with a chitosan salt to produce a film is disclosed in U.S. Pat. No. 3,962,158. Other references to the use of chitosan with other types of material to form wound dressings are disclosed, for example, in U.S. Pat. Nos. 3,632,754 and 4,570,629.

While all of these chitosan patents disclose the use of chitosan in combination with certain conventional materials for the production of wound dressings and other surgical materials, none disclose its combination with a super absorbent polymer which is bound into a latex foam. The combination of these materials provides significantly improved materials over prior art products.

Accordingly, it is an object of this invention to prepare latex foams containing within their structure both water absorbent polymers and chitin biopolymers.

It is a further object of this invention to disclose water absorbent latex foams which contain both water absorbent polymers and chitin biopolymers within their structure which are useful for the absorbance of fluids while retaining the shape of the latex foam.

It is a still further object of this invention to disclose a process for preparing latex foams containing both water absorbent polymers and chitin biopolymers wherein the latex foam has secured thereto a backing to form a water absorbent latex foam laminate containing chitin.

It is a still further object to this invention to disclose a process for preparing a latex foam containing both water absorbent polymers and chitin biopolymers which can be useful as wound or surgical dressings.

These and other objects, as well as the scope, nature, and utilization of this invention, will be apparent from the following detail description.

SUMMARY OF INVENTION

In accordance with the present invention there is provided a water absorbent polymer latex foam containing both a super absorbent polymer and chitin which is produced by the following steps:
a. preparing a foamable latex polymer material;
b. foaming said latex polymer material;
c. blending both a water absorbent polymer and chitin with the latex foam material; and
d. drying the latex foam material containing both the water absorbent polymer and chitin within its structure to form a water absorbent latex polymer foam containing chitin.

The products produced by this process can be highly useful in those areas where the combination of high water absorbance with a wound treating biopolymer is critical, such as for use as wound dressings, surgical dressings, and packaging material for biological materials and the like. In addition, this product can be combined with a porous cover sheet to permit the water absorbing latex foam to draw fluid through the porous cover sheet into the water absorbent material and form a laminated material. This product not only absorbs moisture, but when backed with a liquid impermeable product, keeps the moisture away from the outside surface of the product. This product can have important applications in medical practice.

DETAILED DESCRIPTION OF INVENTION

The water absorbent polymers used in the instant invention are solid, water insoluble but water swellable polymers which are capable of absorbing many times their own weight of water or aqueous solutions. These products are polymers of water soluble acrylic or vinyl monomers which are slightly cross-linked with a polyfunctional reactant. Such cross-linked polymers include polyvinylpyrrolidone, sulfonated polystyrene, polysulfoethyl acrylate, poly(2-hydroxyethylacrylate), polyacrylamide, polyacrylic acid, partial and complete alkali metal salts of polyacrylic acid, and the like. Also included are starch modified polyacrylic acids and hydrolyzed polyacrylonitrile and their alkali metal salts.

Useful water absorbing polymers can be made by polymerizing acrylic acid and starch in an aqueous medium using a polyfunctional monomer, e.g., N,N-alkylene-bis-acrylamide, as the crosslinking agent. This process is described in U.S. Pat. No. 4,076,663, which is incorporated by reference. Water absorbing polymers can also be made as described in U.S. Pat. No. 4,340,706, incorporated by reference, by the inverse polymerization of acrylic acid followed by crosslinking with a polyfunctional component, e.g., epichlorohydrin. Other water absorbing polymers and processes for their manufacture are disclosed, for example, in U.S. Pat. Nos. 4,654,039; 3,669,103 and 3,670,731. All of the aforesaid patents are hereby incorporated by reference.

The water absorbing polymers particularly useful in this invention are those described in U.S. Pat. No. 4,076,663. These water absorbing polymers have a particle size from about 0.5 micron to about 1,000 microns and are capable of absorbing at least about 15 times their weight of an aqueous fluid. In a preferred embodiment superior absorption capabilities exist where the water absorbing polymer particles are less than about 30 microns in size. It is most preferred that the water absorbent polymer particles are reduced to a fine powder wherein said particles are preferably less than about 5 microns in size. These particles show aqueous absorbance capability in excess of 35 times their weight.

These water absorbing polymer particles swell when they absorb aqueous fluids. The particles maintain their approximate shape and geometry but the dimensions thereof are greatly enlarged.

In preparing the articles of this invention, the water absorbing polymers may also be mixed with other particulate materials which are insoluble in water and organic liquids which are capable of absorbing or adsorbing liquids.

Once the water absorbent polymer is prepared, it is blended with a foamed latex material. Any conventional latex can be used in the preparation of the water absorbent polymer latex foam. For example the latex can be selected from the group consisting of acrylic, styrene-butadiene rubber, polyethylene, vinyl acetate, vinyl acetate/acrylic copolymers, polyvinyl chloride copolymers, nitriles, vinyl acetate homopolymers and styrene acrylic polymers, with acrylic or styrene-butadiene rubber latex the preferred latex material.

The preferred latex foam has a low water and high air content. In a preferred embodiment the percentage of water in the latex foam is less than about 60 percent.

Prior to foaming there can be added to the latex certain foaming agents to enhance the foaming ability of the latex or to add crosslinking or other specific traits to the foam structure. Any conventional latex foaming agent or crosslinking agent can be used such as ammonium stearate, phosphate esters, ethoxylated alcohols, azodicarbonamide, sodium laurel sulfate, sulfosuccinamates and mono-ester sulfosuccinates. Preferable latex foaming agents include sodium laural sulfate and sulfosuccinamates.

Prior to the foaming of the foamable latex polymer, additional products may also be added to the foamable latex such as surfactants, fillers or non-woven fibers to enhance further the latex foam's properties. For example, to assist in surface absorption, surfactants such as Pluronic-type surfactants may be added prior to the foaming operation. These products will enhance the capability of the latex foams in their absorbance by increasing the rate at which the water passes through the surface of the foam.

The latex material is foamed by any conventional foaming procedure and preferably is foamed by mechanical means using commercially available equipment manufactured by companies such as Oakes, Latex Equipment Sales and Services, XKG (Reddy, Pa.) or Gaston County Sales and Services Corporation (Stanley, N.C.).

The thickness of the latex foam can be any conventional thickness used in conventional latex foams. However, in a preferred embodiment the thickness of the foam should be less than about 100 mls. By limiting the thickness of the foam to less than 100 mls, the latex foam will maintain high water absorbency. When the thickness of the latex foam exceeds about 100 mls, the water absorbent capabilities of the foam may be reduced or the time of absorption may be increased.

After the latex material is foamed, the water absorbing polymer materials and the chitin are blended with the latex foam. Any conventional method of blending known in the industry can be used for the blending of the water absorbent polymer materials and the chitin with the latex foam. For example, the water absorbent polymer and the chitin can be mechanically blended into the foam. However, in a preferred embodiment, the water absorbent polymer particulates and the chitin, preferable in particulate form, are sprayed into the latex foam which has been cast onto a non-woven substrate. To effect the spraying of the water absorbent particles and the chitin particulates, the particulates are suspended in the spraying medium, such as air, nitrogen or other gaseous environment, and then under pressure transported to a conventional spray nozzle. The water absorbent polymer and chitin particulates are then sprayed into the latex foam. The water absorbent particulates and chitin particulates are anchored to the foam by the spraying process by penetrating the surface of the foam and becoming embedded in the foam structure. This procedure distributes the water absorbent particulates and chitin particulates evenly throughout the structure of the latex foam.

The chitin particulates may also be sprayed into the latex foam in a liquid solution. Conventional procedures for the spraying of a liquid solution are well known in the industry and are similar to those for the spraying of particulates.

When mixing the water absorbent polymer with the foamed latex polymer, the percentage of the water absorbent polymer in relation to the foamed latex polymer may vary depending upon the degree of fluid absorption that is desired. Obviously the greater the percentage of water absorbent polymer within the latex foam, the greater the absorbent capabilities of the latex foam. However, when the percentage of the water absorbent polymer is too high, i.e. greater than about 75 percent, the structure of the latex foam begins to fall apart. Thus, in a preferred embodiment the percentage of water absorbent polymer within the water absorbent polymer latex foam should be from about 5 to about 45 percent and preferably from about 5 to about 25 percent of the overall structure.

The percentage of the chitin particulates in relation to the latex foam may also vary. In addition, the relationship between the amount of the water absorbent polymer and the chitin biopolymer may vary depending upon the particular uses of the material. Obviously, the greater the percentage of the water absorbent polymer, the greater the absorbent capability of the latex foam. In addition, it is apparent that the final product will have increased medical benefits if the percentage of the chitin in the foam is at least about 5 percent of the latex foam. However, when the combined percentage of the water absorbent polymer and the chitin is too high, i.e. greater than about 75 percent, the structure of the latex foam begins to fall apart. Thus, in a preferred embodiment, the percentage of the chitin within the latex foam should be from about 5 to about 35 percent, and preferably, from about 5 to about 20. In addition, the total percentage in the latex foam of the water absorbent polymer and the chitin should be about 5 to about 35 percent.

In prior art water absorbent composites, water absorbent materials and chitin particulates have been generally distributed through a fibrous web with no chemical or physical means for attachment. This technique generated areas in the composite which did not contain water absorbent or chitin materials, thus reducing the absorbency of the overall product. The instant procedure for producing water absorbent latex foams containing chitin provides evenly distributed cellular residence for the water absorbent polymer particulates and chitin particulates within the foam. In addition, the method of the instant invention allows a one-step continuous process for combining a latex foam containing both water absorbent polymer particulates and chitin particulates.

Following blending of the water absorbent polymer and chitin in the latex foam, the latex foam is dried in a conventional drying oven, preferably a hot air oven, at temperatures less than about 200° C. until sufficient water has been driven off, i.e. for a period of about 15 seconds to 2 minutes depending on the temperature of the oven and the thickness of the foam material.

The latex foam containing both the water absorbent polymer and the chitin may be used alone or it may be secured to a non-woven substrate. Any conventional non-woven substrate can be used which will adhere or stay in contact with the latex foam. The preferred substrate onto which is cast the latex foam material is a flexible fabric which is permeable to liquid and can be bound easily to the latex foam material. The fabric can be made of any of the well known textile materials such as cotton, wool, rayon, acetate, acrylic, propylene, copolypropylene, polyester, nylon etc. with the preferred materials including polyesters, polypropylenes and nylons. The fabric can be woven or knitted, though non-woven materials such as those made by the chemical and mechanical bonding of dry laid webs, by wet processing using modified paper making techniques or spin bonding techniques are preferred. Of the non-woven materials, spun bonded fabrics are more preferable. In addition, the material of this layer can be produced from combinations of porous materials such as the combination of polyesters and cotton. This material exhibits good wicking qualities to transfer fluid through the material to the latex foam layer.

In addition to bonding the water absorbent latex foam containing chitin to a conventional non-woven substrate, a generally liquid impermeably material may also be secured against the latex foam. This impermeably layer will prevent the flow of a liquid through the latex foam. This impermeable layer can be made of any of the well known impermeable materials such as polyethylene or polypropylene film. See for example the material disclosed in U.S. Pat. No. 4,731,066. Certain "breathable" impermeable materials may also be used which have been disclosed, for example, in U.S. Pat. No. 4,713,068. In addition, certain microporous materials such as Celgard ®, manufactured by Hoescht Celanese, which contains microporous structures which allow the material to be liquid impermeable while still permitting the release of certain gases from the second layer are also permissible. See, for example, U.S. Pat. Nos. 3,156,242, 3,426,754 and 4,347,844.

These composite layers can be bound together by any conventional bonding procedure including needle punch, air laid, resin bonded or melt bonded. For example, any conventional adhesive web material which will allow the materials to retain their flexibility and water permeability can be used to bind the layers together.

The latex foam with both water absorbent polymers and chitin blended in their structure shows significant water absorbance depending on the thickness of the latex foam and the percentage of water absorbent polymer contained within the structure. With about 5 percent water absorbent polymer and 5 percent chitin within the latex foam structure, the distilled water absorbence of the material is at least about 75 times the weight of the water absorbent polymer and at least about 10 times the weight of the water absorbent polymer in a one percent saline solution. When percentages of the water absorbent polymer in the latex foam approach 25 percent and the percentage of the chitin is 25 percent, the absorption of distilled water increases to about 80 times the weight of the water absorbent polymer and up to about 10 times its weight in a one percent saline solution.

The following examples are given as specific illustrations of the invention. All parts and percentages are by weight unless otherwise stated. It is understood however that the invention is not limited to specific details set forth in the examples.

EXAMPLE

A styrene-butadiene rubber (SBR) latex foam was cast on a wet-lay non-woven substrate. The SBR latex chosen was Unocal #83026, a hydrophilic SBR latex. Using a conventional stirring mechanism, 200 grams of SBR latex was foamed until the ratio of air to SBR latex was about 7:1. The SBR latex was agitated for about 3 to 4 minutes.

The substrate used to support the foam was a wet lay web comprised of 80 percent polyester and 20 percent wood pulp. Following the drying of this wet-lay web, the foamed SBR latex was spread while still wet on the substrate. Three different thicknesses of the SBR latex were prepared, respectively 20 mls, 40 mls and 80 mls. After the SBR latex was spread and the thickness was set, the water absorbent polymer was sprayed by a Nordson Air Fluidized Powder Spray apparatus into the SBR latex. The water absorbent material was a graft copolymer of about 91 percent acrylic acid and 9 percent oxidized starch, crosslinked with 0.1 percent N,N'-methylene-bis-acrylamide made by the process described in U.S. Pat. No. 4,076,663. The water absorbent material comprised respectively 5 to 10 percent, 15 to 20 percent and 20 to 25 percent of the SBR latex mixture. The particulate size of the water absorbent material was generally less than about 30 microns.

Following the spraying of the water absorbent polymer, chitosan particulates were also sprayed onto the latex. The chitosan was purchased from Protan Laboratories, Inc., Redmond, Va. The chitosan particles comprised respectively 5 percent, 10 percent and 15 percent of the SBR latex mixture. The particulate size of the chitosan was generally about 350 microns.

After the water absorbent polymer particulate and the chitosan particulate were sprayed on to the SBR latex foam, the material was dried in an oven at 250° F. for approximately 15 to 20 seconds to 5 minutes. After the drying of the SBR latex material, tests were run on the foam to determine its absorbency in both distilled water and a 1 percent saline solution. Results of these test are shown on Table I.

TABLE I

| WATER ABSORBENT SBR LATEX FOAM | | | |
|---|---|---|---|
| Water Absorbant polymer percentage | 5-10 | 15-20 | 20-25 |
| THICKNESS, mls. | 20 | 40 | 80 |
| CHITOSAN percentage | 5 | 10 | 15 |
| STATIC LIQUID ABSORPTION DISTILLED WATER % by weight | 3500 | 4500 | 6500 |
| 1% SALINE SOLUTION % by weight | 1200 | 1000 | 1400 |

As is apparent from these result, latex foams containing both water absorbent polymers and chitin which absorb a large amount of water in relation to the weight of the foam can be produced. Latex foams of this type can be prepared using various types of substrates, various amounts of the water absorbent polymer and chitin and having different thicknesses. These foams will have great utility because of their high degree of water absorbence in comparison with conventional latex foams.

What is claimed:

1. A water absorbent latex polymer foam containing chitin prepared by the process of:
   a. preparing a foamable latex polymer material;
   b. foaming said latex polymer material to form a latex foam material;
   c. blending both water absorbent polymer products and chitin products with the latex foam material; and
   d. drying the latex foam material containing the water absorbent polymer and chitin within its structure to form a water absorbent latex polymer foam containing chitin.

2. A water absorbent latex polymer foam containing chitin prepared by the process of;
   a. preparing a styrene-butadiene rubber latex polymer material;
   b. foaming said styrene-butadiene rubber polymer material to form a styrene-butadiene rubber latex foam;
   c. blending both water absorbent polymer particulates and chitin particulates with the styrene-butadiene rubber latex foam; and
   d. drying the styrene-butadiene rubber foam material containing within its structure both the water absorbent polymer particulates and chitin to form a water absorbent styrene-butadiene rubber latex foam containing chitin within its structure.

3. The water absorbent latex polymer foam containing chitin of claim 1 wherein the water absorbent polymer comprise about 5 to 45 percent of the structure of the foam material.

4. The water absorbent latex polymer foam containing chitin of claim 2 wherein the water absorbent polymer particulates comprise about 5 to 45 percent of the structure of the foam material.

5. The water absorbent latex polymer foam containing chitin of claim 1 wherein the water absorbent polymer comprise about 5 to 25 percent of the structure of the foam material.

6. The water absorbent latex polymer foam containing chitin of claim 2 wherein the water absorbent polymer particulates comprise about 5 to 25 percent of the structure of the foam material.

7. The water absorbent latex polymer foam containing chitin of claim 1 wherein the chitin comprises about 5 to 35 percent of the structure of the foam material.

8. The water absorbent latex polymer foam containing chitin of claim 2 wherein the chitin comprises about 5 to 35 percent of the structure of the foam material.

9. The water absorbent latex polymer foam containing chitin of claim 1 wherein the chitin comprises 5 to 20 percent of the structure of the foam material.

10. The water absorbent latex polymer foam containing chitin of claim 2 wherein the chitin comprises 5 to 20 percent of the structure of the foam material.

11. A water absorbent latex polymer foam product containing chitin prepared by the process of:
   a. preparing a foamable latex polymer material;

b. foaming said foamable latex polymer material to form a latex foam material;
c. blending both water absorbent polymer products and chitin with the latex foam material; and
d. drying the latex foam material containing both the water absorbent polymer products and chitin within its structure to form a water absorbent latex foam containing chitin; and
e. securing the water absorbent latex foam containing chitin to a substrate to form a water absorbent latex polymer foam containing chitin which is secured to a substrate.

12. A water absorbent polymer foam product containing chitin prepared by the process of:
a. preparing a styrene-butadiene rubber latex polymer material;
b. foaming said styrene-butadiene rubber latex polymer material to form a styrene-butadiene rubber latex foam;
c. blending both water absorbent polymer particulates and chitin with the styrene-butadiene rubber latex foam;
d. drying the styrene-butadiene rubber latex foam containing water absorbent polymer particulates and chitin to form a water absorbent styrene-butadiene rubber latex foam containing chitin; and
e. securing the styrene-butadiene rubber latex polymer foam containing water absorbent polymer particulate and chitin to a non-woven substrate to form a water absorbent styrene-butadiene rubber latex polymer foam containing chitin which is secured to a substrate.

13. The water absorbent polymer foam material containing chitin of claim 1 wherein the size of the water absorbent particulates are from about 0.5 micron to about 1,000 microns.

14. The water absorbent polymer foam material containing chitin of claim 2 wherein the size of the water absorbent particulates are from about 0.5 micron to about 1,000 microns.

15. The water absorbent polymer foam material containing chitin of claim 11 wherein the size of the water absorbent particulates are from about 0.5 micron to about 1,000 microns.

16. The water absorbent polymer foam material containing chitin of claim 12 wherein the size of the water absorbent particulates are from about 0.5 micron to about 1,000 microns.

17. The water absorbent polymer foam material containing chitin of claim 1 wherein the water absorbent products are particulates whose size are less than about 20 microns.

18. The water absorbent polymer foam material containing chitin of claim 2 wherein the size of the water absorbent particulates are less than about 20 microns.

19. The water absorbent polymer foam material containing chitin of claim 11 wherein the size of the water absorbent particulates are less than about 20 microns.

20. The water absorbent polymer foam material containing chitin of claim 12 wherein the size of the water absorbent particulates are less than about 20 microns.

21. The water absorbent latex polymer foam containing chitin product of claim 11 wherein the substrate is a non-woven fabric prepared by spin bonding.

22. The water absorbent latex polymer foam containing chitin product of claim 12 wherein the substrate is a non-woven fabric prepared by spin bonding.

23. The water absorbent latex polymer foam containing chitin of claim 1 wherein the latex is selected from the group consisting of acrylic latex, styrene-butadiene rubber latex, polyethylene latex, vinyl acetate latex, vinyl acetate/acrylic copolymer latex, polyvinyl chloride latex, nitrile latex, vinyl acetate latex and styrene acrylic latex.

24. The water absorbent latex polymer foam containing chitin of claim 11 wherein the latex is selected from the group consisting of acrylic latex, styrene-butadiene rubber latex, polyethylene latex, vinyl acetate latex, vinyl acetate/acrylic copolymer latex, polyvinyl chloride latex, nitrile latex, vinyl acetate latex and styrene acrylic latex.

25. A water absorbent latex foam material containing chitin prepared by blending water absorbent polymer particulates and chitin with a foamable latex, wherein the water absorbent polymer particulates comprise at least about 5 percent of the latex foam material, and wherein the material is capable of absorbing at least about 75 times the weight of the water absorbent polymer particulates in water and about 10 times the weight of the water absorbent polymer particulates in a one percent saline solution.

* * * * *